(12) United States Patent
Hewes et al.

(10) Patent No.: US 7,825,356 B2
(45) Date of Patent: Nov. 2, 2010

(54) HEATER FOR ASSISTING IN VENOUS CATHETERIZATION

(75) Inventors: Karen Hewes, Stillwater, MN (US); Scott D. Augustine, Bloomington, MN (US); Mark C. Albrecht, Minneaoplis, MN (US); Randall C. Arnold, Minnetonka, MN (US); Thomas F. Neils, Minneapolis, MN (US)

(73) Assignee: Augustine Biomedical and Design LLC, Eden Prairie, MN (US)

( * ) Notice: Subject to any disclaimer, the term of this patent is extended or adjusted under 35 U.S.C. 154(b) by 792 days.

(21) Appl. No.: 11/537,065

(22) Filed: Sep. 29, 2006

(65) Prior Publication Data

US 2007/0068932 A1 Mar. 29, 2007

Related U.S. Application Data

(60) Provisional application No. 60/722,241, filed on Sep. 29, 2005, provisional application No. 60/722,256, filed on Sep. 29, 2005.

(51) Int. Cl.
*H05B 3/10* (2006.01)
*A61F 7/00* (2006.01)

(52) U.S. Cl. ............... 219/552; 219/211; 219/212; 219/528; 219/529; 219/544; 219/545; 219/546; 219/549; 219/553; 219/530; 219/535; 219/522; 219/543; 219/548; 607/109; 607/110; 607/112; 607/114; 126/201

(58) Field of Classification Search ........... 219/211–12, 219/217, 528, 529, 544–6, 549, 552–3, 530, 219/535, 522, 543, 548; 607/108–112, 114; 126/201
See application file for complete search history.

(56) References Cited

U.S. PATENT DOCUMENTS

| 4,747,409 A * | 5/1988 | Silen ..................... 607/108 |
| 4,899,749 A | 2/1990 | Laroco |
| 5,074,285 A | 12/1991 | Wright |
| 5,395,399 A | 3/1995 | Rosenwald |
| 5,496,358 A | 3/1996 | Rosenwald |
| 5,683,438 A | 11/1997 | Grahn |
| 6,149,674 A | 11/2000 | Borders |
| 6,565,593 B2 | 5/2003 | Diana |
| 6,723,115 B1 | 4/2004 | Daly |
| 7,022,950 B2 * | 4/2006 | Haas et al. .................. 219/528 |
| 2004/0193237 A1 | 9/2004 | Krueger |

FOREIGN PATENT DOCUMENTS

| DE | 3343664 C1 | 3/1985 |
| DE | 10065592 A1 | 7/2002 |
| EP | 787476 A2 | 8/1997 |
| WO | 01/35878 A2 | 5/2001 |

OTHER PUBLICATIONS

Bair Hugger brochure at http://www.bairhugger.com/arizanthealthcare/pdf/600755A.pdf.
Henriques, F. C., Studies in thermal injury; The conduction of heat to and through skin and the temperatures attained therein, American Journal of Pathology 23:531-548m 1846.
Lenhardt et al., British Medical Journal 325:409, Aug. 2002.

* cited by examiner

*Primary Examiner*—Shawntina Fuqua
(74) *Attorney, Agent, or Firm*—Fredrikson & Byron, P.A.

(57) ABSTRACT

Certain embodiments pertain to a heater for warming a patient's extremity in order to cause vasodilation for facilitating venous catheterization.

43 Claims, 7 Drawing Sheets

HEATER FOR ASSISTING IN VENOUS CATHETERIZATION

PRIORITY CLAIM

The present application claims priority to provisional application Ser. No. 60/722,241 entitled: DISPOSABLE SLEEVE AND ELECTRIC HEATER FOR ASSISTING IN INTRAVENOUS CATHERIZATION, filed on Sep. 29, 2005 and to provisional application Ser. No. 60/722,256 entitled: HEATING CUFF, also filed on Sep. 29, 2005, each being hereby incorporated by reference in its entirety.

RELATED APPLICATION

The present application is related to the following commonly assigned utility patent application, filed concurrently herewith, and which is hereby incorporated by reference in its entirety: DISPOSABLE SLEEVE FOR ASSISTING IN VENOUS CATHETERIZATION, Ser. No. 11/537,081.

BACKGROUND

Catheterization of human veins with needles and catheters is a common medical procedure. Clinicians frequently need to access patients' veins in order to draw blood for laboratory testing or for placement of intravenous (IV) catheters, for the administration of medicines, fluids or blood.

Catheterization is typically accomplished by placing a rubber tourniquet around an extremity, for example a forearm, proximal to the planned point of catheterization. The tourniquet causes compression of the superficial veins without compressing the associated arteries. Therefore, the blood is pumped through the arteries past the tourniquet into the distal extremity. Since the veins are compressed, the blood is prevented from returning to the heart. The veins typically dilate due to the increased intravascular pressure and are thus more visible and easier to access with the needle or catheter. Once the dilated vein is identified, the skin is cleaned and usually numbed with a local anesthetic. The needle or catheter is then inserted into the dilated vein.

Catheterization can be difficult to accomplish in infants and children, obese patients, patients with darker skin, IV drug abusers and patients receiving chemotherapy for cancer. Additionally, any patient can be difficult to cannulate if he or she is cold, frightened, apprehensive or dehydrated. This commonly occurs in patients that are injured or are about to undergo surgery. In these situations, veins are actively constricted by the sympathetic nervous system and, therefore, will not dilate in response to an increase in intravenous pressure. Even the application of a tourniquet may not cause the veins to visibly dilate.

It has been known that application of heat to the skin of a forearm helps to reduce vasoconstriction and dilate veins. Traditionally, heat has been applied by soaking towels in warm water and then wrapping the towel around a forearm. However, the use of wet towels has several significant drawbacks. The wet towels quickly cool. The wet skin experiences an evaporative heat loss that may actually cool the skin. The water is messy and may cause the skin to macerate. Therefore, the use of we towels has many significant deficiencies in effectiveness and convenience.

Electric heating pads have also been used for heating the skin of the forearm to aid IV catheterization. Electric heating pads do not have the cooling and messy problems associated with wet towels. However, electric heating pads may not be hot enough to achieve rapid vasodilation. If they are hot enough, the high temperature may inadvertently be applied for too long, risking thermal injury. Electric heating pads are difficult to wrap snuggly around the forearm and, therefore, typically do not maintain good contact with the skin for optimal conductive heat transfer.

Forced air patient blankets such as the Bair Hugger® blanket (distributed by Arizant Inc., Eden Prairie, Minn.), have also been used to warm the arms of patients for starting IVs. Such blankets are wrapped around a patient and then inflated with warm, forced air. However, the warm air cools inside of the blanket and does not remain warm enough to cause rapid vasodilation. Clinicians have attempted to avoid this cooling of forced air by blowing warm air directly onto a patient without using a blanket (a process known as "hosing"). However, hosing is not recommended because the direct contact of warm air with skin increases the risk of thermal burns. Moreover, the forced air is supplied by noisy blowers that are relatively energy-inefficient and complicated.

A loose fitting mitt made of carbon fiber conductive fabric has also been used. Lenhardt et al. published a study (in British Medical Journal 325:409, August 2002) that evaluated the effectiveness of such a loose fitting mitt. The mitt was heated to 52° C. and applied to patients for 15 minutes prior to starting an IV. The success rate for catheterization was 94% compared to 72% for an unheated control group. Warming the hand and forearm with a loose fitting mitt appeared to be useful for improving the success rate of catheterization. However, the required 15 minutes of warming time may be too long to be practical in clinical settings. In addition, an increase in temperature could subject the patients to a risk for thermal burn injuries. Additionally, the loose fitting mitt does not optimize conductive heat transfer to the skin because it does not conform to the skin to maximize skin-heater contact.

The prior art heaters have several drawbacks. Some of the heaters have rigid structures or loose fitting structures, which are undesirable because they do not conform to a patient's extremity. For example, a patient with a smaller arm may not have very much skin in contact with a loose fitting or rigid heater. This prevents optimal heat conductive heat transfer between the heater and the skin. Some of the heaters are also unnecessarily complicated and include a variety of support structures, chambers, forced air devices, suction devices and the like. Complicated heaters are difficult to apply to a patient during a clinical setting and delay the overall dilation time. Complicated heaters may also intimidate a patient.

Prior art heaters either do not heat at temperatures or lengths of time appropriate for rapid venous dilation, which is beneficial in a clinical setting. For instance, some prior art heaters heat at too low of temperatures or for insufficient lengths of time. The heaters also do not include a timing device to limit the duration of exposure to heat, thereby increasing the risk of thermal injury to a patient's skin. In addition, some of the heaters are provided in direct contact with a patient's extremity and must be cleaned between patients to avoid cross-contamination. A patient's bodily fluids may contaminate the heater and must be cleaned before the heater is used on the next patient. The cleaning of medical equipment is both expensive and inefficient.

There is a need for an improved heater that is simple to apply, is easy to clean, achieves rapid dilation, optimizes heat transfer, and/or reduces the risk of thermal injury. Certain embodiments of the invention described below solve one or more of the limitations of the prior art described above.

SUMMARY

Certain embodiments pertain to a heater for warming a patient's extremity in order to cause vasodilation for enhancing venous catheterization. Such a heater can also be used for improving venous blood flow during chemotherapy. Additionally, such a heater can be used for causing vasodilation and optimizing blood flow in patients with Reynaud's disease, post vascular surgery, skin grafting, appendage reattachment surgery, post-hemodialysis, blood donation, wound treatment, or other situations. Certain embodiments optimize the conductive heat transfer, allowing the temperature of a heating device to be minimized, thereby reducing the risks of thermal burns, and allowing the heating time to be reduced, thereby improving the practicality and effectiveness of the device.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention.

Figure 1:
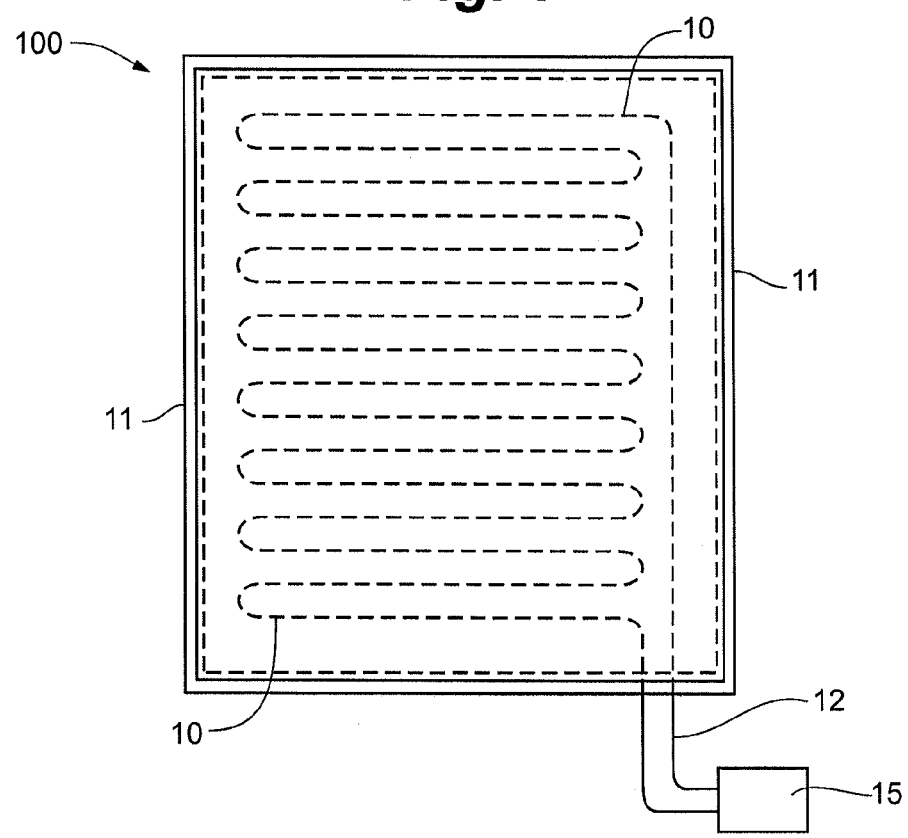
FIG. 1 is a top view of a heater according to an embodiment.
Figure 2:
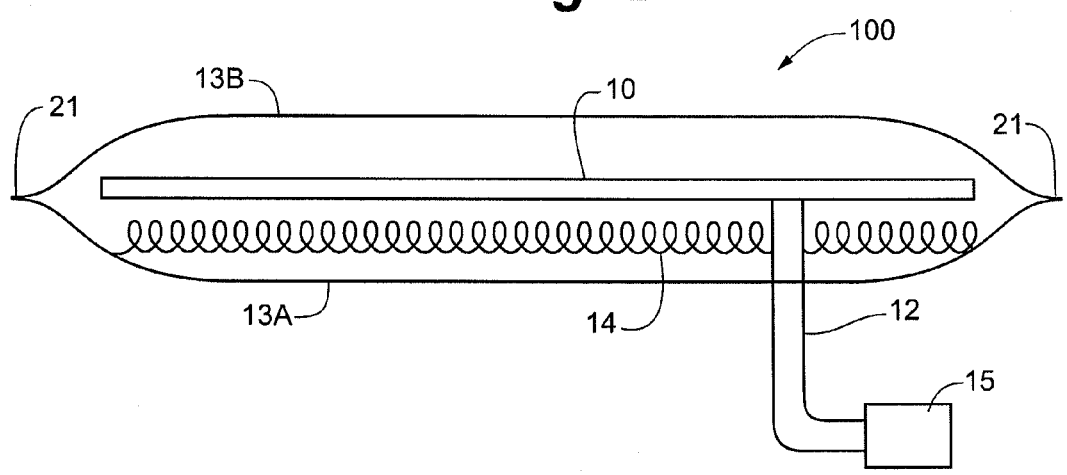
FIG. 2 is a section view of a heater according to an embodiment.

FIGS. 1-2 illustrate a heater 100 according to one embodiment. The heater 100 includes a heating element 10 enclosed between a first layer 13A and a second layer 13B. The layers 13A, 13B are sealed together about a generally rectangular perimeter 11 to hold the heating element 10 therebetween. While the illustrated perimeter 11 is shown as a rectangle, the perimeter can have any suitable size and shape to accommodate the length of an extremity, for example a patient's forearm and hand. The layers 13A, 13B can be sealed together using any mechanism known in the art. In some cases, the heating element 10 is embedded in, or attached to, one of the layers 13A, 13B. The layers 13A, 13B are comprised of any material. In some cases, the layers 13A, 13B are made of a water-resistant or water-proof material. An antimicrobial substance can be provided on the layers 13A, 13B to prevent the spread of germs between patients. Examples of antimicrobial substances include but are not limited to metals such as silver or copper and other antimicrobial chemical agents.

The heating element 10 may comprise any heating mechanism known in the art. In most cases, the heating element 10 includes a flexible material, for example a flexible wire. In the illustrated embodiment, the heating element 10 is a single wire (e.g., an electrically resistive wire) routed throughout the area of the heater. Of course, the element 10 can alternately be a matrix of wires. Likewise, other resistive heating elements can be employed, examples of which include, but are not limited to carbon fiber and carbonized fiber fabrics and other conductive fabrics such as those coated with conductive materials such as polypyrrole or conductive inks. In some cases, fabric incorporates a matrix of wires or closely spaced conductive heating elements.

In some embodiments, the heater 100 is used with a forearm and hand, and the heat element 10 is configured so that it has a watt-density greater in the area in contact with the forearm compared to the area in contact with the hand. The forearm has a greater mass than the hand and therefore acts as a greater heat-sink. Increasing the watt-density to the forearm optimizes the heat transfer to both areas.

A cord 12 extends from heating element 10 to a unit 15 that includes a temperature control and power source. The temperature control can include one or more temperature settings and a timer for the temperature settings. At least one of the temperature settings is set high enough to achieve rapid venous dilation and the timer is set to prevent that high setting from being applied so long as to cause thermal injury. In some cases, the high temperature setting is at least 52° C. and the timer has a time period of less than 15 minutes for the high setting.

The relatively high temperature causes more rapid and effective vasodilation without risks of thermal injury. The susceptibility of skin to thermal injury is determined by the combination of temperature and time. High temperatures are tolerated for short periods of time. The skin temperature does not come close to equilibrating with the temperature of the heater during the short heating period. For example, when the heater is applied to a forearm, the thermal mass of the tissue in the forearm and hand act as a heat sink and the blood flow rapidly removes the excess heat. Additionally, there is a high degree of thermal resistance between the heater and the skin as compared to the thermal resistance between the skin surface and the deeper layers of tissue which is blood flow regulated.

In one embodiment, the temperature control includes a first temperature setting. The unit 15 is also provided with a timer that is configured to maintain the first temperature setting for a given time period. A switch is also provided on the unit 14 that is coupled to the temperature control and is configured to switch from the first temperature setting to an off setting or to an optional second temperature setting when the time period expires. The optional second temperature setting is lower than the first temperature setting. The first temperature setting can be between about 52° C. and about 70° C., for example about 60° C. The optional second temperature setting can be between about 40° C. and about 50° C., for example about 45° C. The time period can be less than about 15 minutes to avoid thermal damage to the forearm. In some cases, the time period is in a range extending from about 7 minutes to about 10 minutes. In other cases, the time period is less than 15 minutes. Once the time period expires, the first temperature setting switches to an off setting or to the second temperature setting. The second temperature setting, if used, can maintain the state of vasodilation achieved by the first temperature setting for a period of time that a clinician may need to, for example, set up an IV. In some embodiments, a signal is provided (e.g., a light or sound) on the unit 15 to alert a clinician when the time period for the first temperature setting is complete.

The unit 15 and described temperature control system can be used with any appropriate heater known in the art, not just the illustrated heater. In some embodiments, a clinician places a heater having the described temperature control system over an extremity and heats a heating element of that heater to a first temperature for a given time period. Once the given time period expires, the clinician turns the element off or heats the element to a second temperature, the second temperature being lower than the first temperature. The first temperature setting can be between about 52° C. and about 70° C., for example about 60° C. The optional second temperature setting can be between about 40° C. and about 50° C., for example about 45° C. The time period can be less than about 15 minutes or less than about 10 minutes to avoid thermal damage to the forearm.

With reference to FIG. 2, a compressible material 14 can be disposed between the heating element 10 and one of the layers 13A, 13B. In some embodiments, the compressible material 14 is positioned between the element 10 and the layer which is not in contact with the patient extremity. For example, in FIG. 2, layer 13A serves as an outer layer and layer 13B serves as an inner layer in contact with the patient extremity. Examples of suitable compressible materials include but are not limited to foam rubber, foam plastic and a high loft nonwoven polymeric material.

When the heater 100 is secured around the extremity, the compressible material 14 presses against the heating element 10 and presses it into closer contact with the skin. This close contact with the skin optimizes conductive heat transfer from the element 10 to the skin and optimizes the efficiency of the heat transfer for any given temperature. The efficient heat transfer allows the heater to be operated at lower temperatures and still be clinically effective. The close contact also maximizes the uniformity of the temperature across the heater. This is important because areas of the heater that do not contact the skin can undesirably become excessively hot. The compressible material 14 also helps to make the fit more comfortable for the patient.

Alternately, or additionally, the heater 100 can include a heat permeable standoff material (not shown), to diffuse heat from heating element 10 towards the layer 13B in contact with the extremity. For example, a metal foil can be provided.

Figure 3:
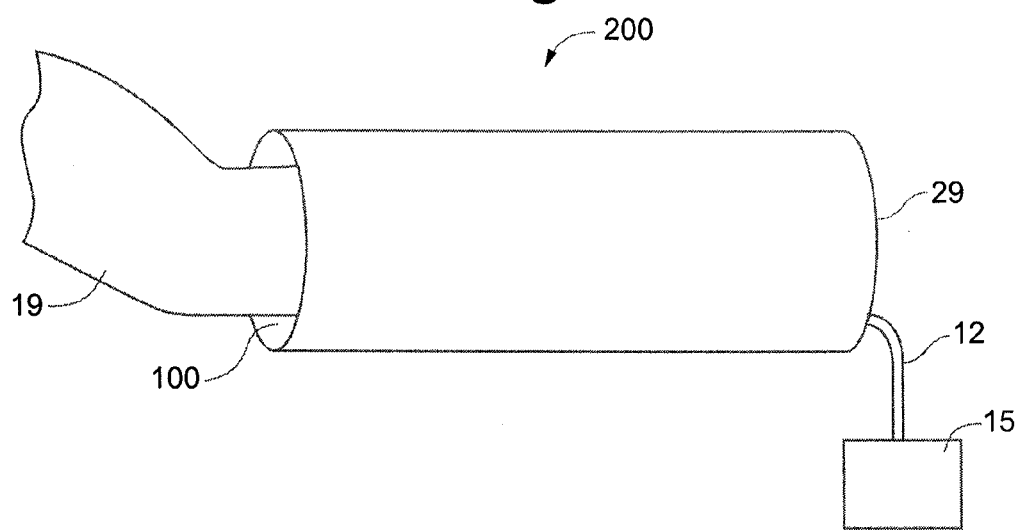
FIG. 3 is a side perspective view of a heater formed as a heating cuff and arranged on an extremity according to an embodiment.
Figure 4:
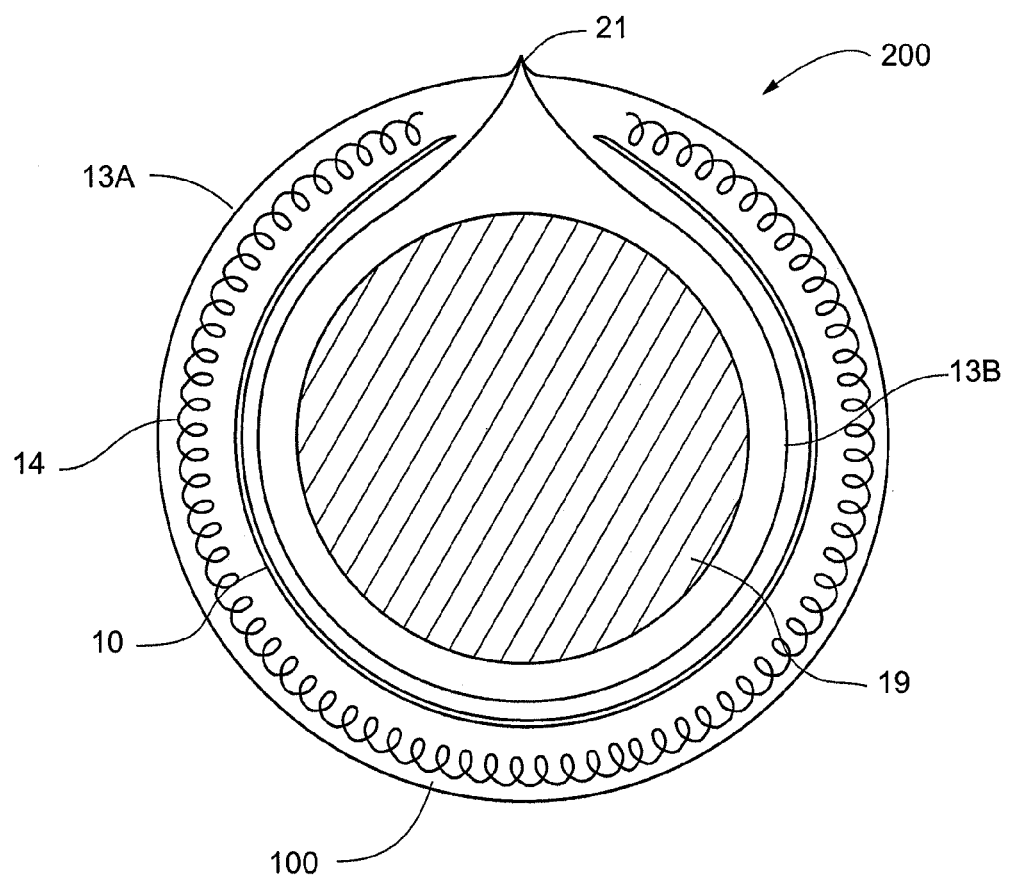
FIG. 4 is a cross-section view of a heating cuff having its sides connected together according to an embodiment.

FIG. 3 illustrates a heater 100 that has been rolled into a cuff 200, which encloses an extremity 19 in a generally tubular cavity. The cuff can be held in place around the extremity 19 using any known mechanism. For example, FIG. 4 illustrates an embodiment wherein the side edges 21 of the heater 100 are connected together to form a cuff 200. In some cases, the edges 21 are sewn together to form cuff prior to fitting the cuff onto the extremity. Alternatively, side edges 21 are connected together using reversible fasteners, for example hook-and-loop, snap-fit, button, buckle, ties and adhesive fasteners after having rolled heater 100 about the extremity.

Figure 5:
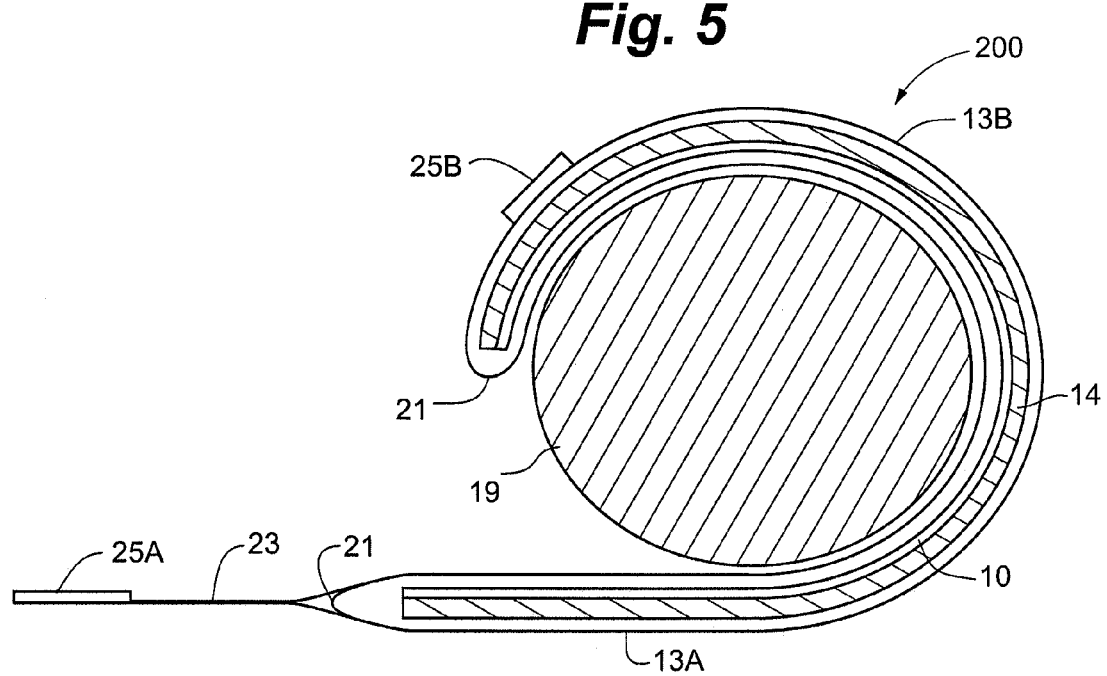
FIG. 5 is a cross-section view of a heating cuff having a flap for connecting its sides together according to an embodiment.

FIG. 5 illustrates an embodiment wherein one side edge includes a flap 23 containing a fastener 25A that connects to a corresponding fastener 25B located on an external part of layer 13A. In some cases, fasteners 25A, 25B are hook-and-loop fasteners. If a compressible material 14 is provided in between the first layer 13A and the heating element 10, the act of connecting and tightening the fasteners 25A, 25B compresses the compressible material 14, which in turn presses the heating element 10 in closer contact with the skin.

In some embodiments, a distal end 29 of the cuff 200 is closed, for example by sewing one or more edges of the distal end together. This creates a cuff that is closed on three sides. The proximal end is left open so that the extremity can be inserted into the cuff.

Figure 6:
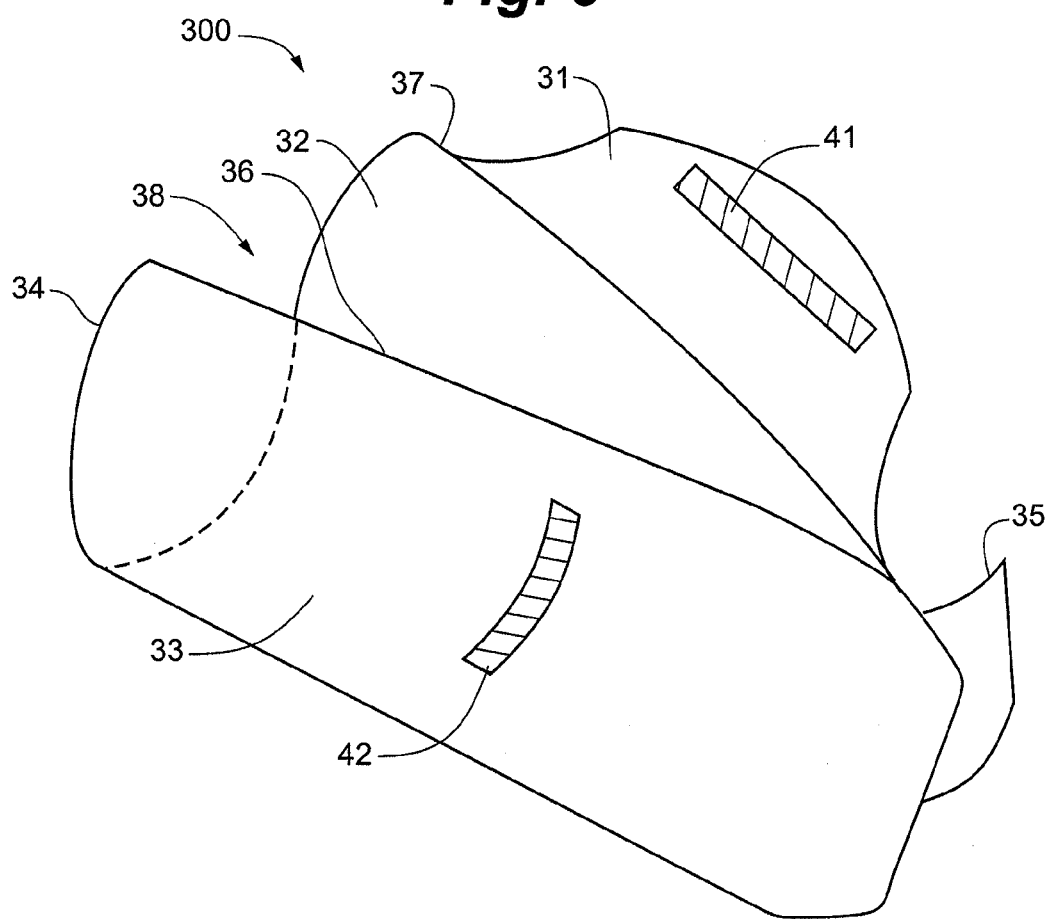
FIG. 6 is a perspective view of a heating cuff according to an embodiment.
Figure 7:
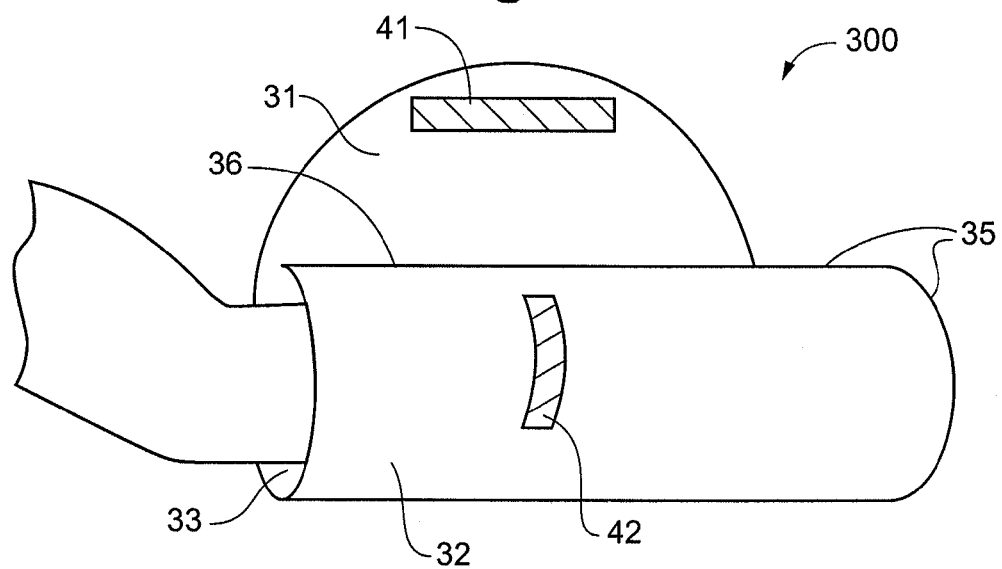
FIG. 7 is a side perspective view of a heating cuff in an unfastened position and arranged on a forearm according to an embodiment.
Figure 8:
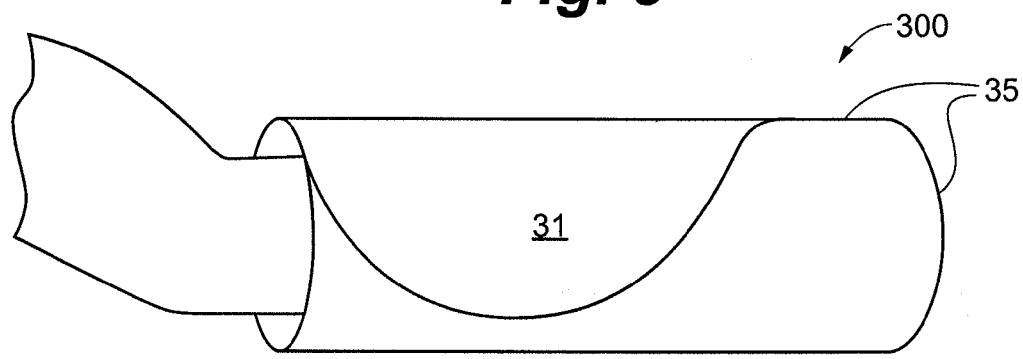
FIG. 8 is a side perspective view of the heating cuff in a fastened position and arranged on a forearm according to an embodiment.

FIGS. 6-8 illustrate a heater formed as a generally tubular cavity or cuff 300 according to one embodiment. Although not shown in these Figures, it should be understood that cuff 300 includes a heating element disposed therein. Again, the heating element can be any heating mechanism element known in the art. In some cases, the heating element is configured according to the embodiments described in conjunction with FIGS. 1-5, although this is not required. The heater design shown in FIGS. 6-8 is advantageous because it is simple and easy to apply to a patient forearm. The heater is also flexible and conforms to any size and shape of forearm. The heater is also designed to completely surround the forearm and hand, in order to optimize the heat transfer and provide for a rapid venous dilation.

FIGS. 6-8 illustrate a heater formed as a cuff 300 including an inner surface 32 and an outer surface 33. A heating element is disposed inside of the cuff 300 in between the outer surface 32 and inner surface 33. According to some embodiments, an additional material, for example a compressible material 14 as described in conjunction with FIGS. 1-5, is also enclosed between the outer surface 33 and the heating element. Likewise, in some embodiments, the inner and outer surfaces 32, 33 can be configured as the layers 13A, 13B described in conjunction with FIGS. 1-5, although this is not required.

The cuff 300 forms a generally tubular cavity 38. A proximal edge 34 of the cuff forms a proximal end opening of cavity 38. Likewise, a first side edge 36 and a second side edge 37 form a closable side opening of the cavity 38. A distal edge 35 is closable and seals the distal end of the cavity 38 to trap a patient's hand within the cavity. A patient inserts his or her hand into the cavity 38 through the proximal end and side openings. Although FIGS. 6-8 illustrate a closed distal edge 35 extending distally from side opening formed by first and second sides 36, 37, and around a distal end of cavity 38, the extent of closed distal edge 35 can vary being either more extensive or less extensive. Closed distal edge 35 can be a bonded or sewn junction or can be a zipper junction. In certain cases, the distal edge 35 is permanently closed.

The second side edge 37 includes a side flap 31 extending laterally therefrom. In some cases, the flap 31 can simply be an extension of the shell 300. The flap 31 wraps over the side edge 36 and is secured to the outer surface 33. The flap 31 and outer surface 33 can be connected together using reversible fasteners, for example hook-and-loop, snap-fit, button, buckle, ties and adhesive fasteners. In the illustrated FIGS. 6-8, the flap 31 is provided with a fastener 41 that connects to a corresponding fastener 42 located on the outer surface 33. In some cases, fasteners 41 and 42 are hook-and-loop fasteners. After the patient's hand is inserted into the cavity 38, the flap 31 is wrapped over side edge 36 and fastener 42A is secured to fastener 42B. After use, the fasteners are released and flap 31 is pulled off the outer surface 33 to expose the internal cavity and provide easy access for cleaning.

Once the cuff 300 is closed, as shown in FIG. 8, the cuff provides insulation to allow for rapid venous dilation. The entire arm and hand is insulated and prevented from exposure to surrounding cool air. The closed distal edge 35 can further prevent cuff 300 from being unwrapped into a rectangular or square shape and inadvertently used as a heating pad for other parts of the body. This is an important safety feature because a high temperature, for example a temperature of at least 52° C., is provided to the heating element in order to achieve rapid venous dilation. This temperature is much higher than the temperatures used in existing heating pads. Heating pads are also commonly left on the body for prolonged periods of time (often more than 15 minutes). It is not recommended to leave a heating pad with temperatures higher than 52° C. on a body part for a prolonged period of time. Thus, the closed distal edge 35 not only insulates the forearm but also helps to prevent using the cuff 300 as a heating pad.

What is claimed is:

1. A heater for heating an extremity of a patient, the heater comprising:
    at least one heating element enclosed within a shell, the shell sized to surround the extremity; and
    a temperature control coupled to the at least one heating element, the temperature control including a first temperature setting and a second temperature setting, the second temperature setting being lower than the first temperature setting, wherein the first temperature setting is in a range extending from about 52 degrees Celsius to about 70 degrees Celsius, and wherein the second temperature setting is in a range extending from about 40 degrees Celsius to about 50 degrees Celsius;
    a timer coupled to the temperature control, the timer configured to maintain the first temperature setting for a given time period; and
    a switch coupled to the temperature control and the timer, the switch configured to switch from the first temperature setting to the second temperature setting when the time period expires.

2. The heater of claim 1 wherein the first temperature setting is about 60 degrees Celsius.

3. The heater of claim 1 wherein the second temperature setting is about 45 degrees Celsius.

4. The heater of claim 1 wherein the time period is less than about 15 minutes.

5. The heater of claim 1 wherein the time period is in a range extending from about 7 minutes to about 10 minutes.

6. The heater of claim 1 wherein the heating element and the shell are each flexible.

7. The heater of claim 1 wherein the flexible heating element and shell are configured to be snugly wrapped around a forearm.

8. A heater for heating an extremity of a patient, the heater comprising:
    at least one heating element enclosed within a shell, the shell sized to surround the extremity; and
    a temperature control coupled to the at least one heating element, the temperature control including a temperature setting, the temperature setting being in a range extending from about 52 degrees Celsius to about 70 degrees Celsius;
    a timer coupled to the temperature control, the timer configured to maintain the temperature setting for a given time period, the time period being less than about 15 minutes.

9. The heater of claim 8 wherein the temperature setting is about 60 degrees Celsius.

10. The heater of claim 8 further comprising a switch for switching from the temperature setting to a second temperature setting, the second temperature setting being lower than the temperature setting.

11. The heater of claim 10 wherein the second temperature setting is in a range extending from about 40 degrees Celsius to about 50 degrees Celsius.

12. The heater of claim 11 wherein the second temperature setting is about 45 degrees Celsius.

13. The heater of claim 10 wherein the time period is in a range extending from about 7 minutes to about 10 minutes.

14. A method for facilitating venous catherization at an extremity of a patient, the method comprising:
    enclosing the extremity within a heating cuff, the heating cuff containing at least one heating element;
    heating the heating element to a first temperature for a given time period;
    heating the heating element to a second temperature when said time period expires, the second temperature being lower than the first temperature, wherein the first temperature is in a range extending from about 52 degrees Celsius to about 70 degrees Celsius and wherein the second temperature is in a range extending from about 40 degrees Celsius to about 50 degrees Celsius.

15. The method of claim 14 wherein the first temperature is about 60 degrees Celsius.

16. The method of claim 14 wherein the second temperature is about 45 degrees Celsius.

17. The method of claim 14 wherein the time period is less than about 15 minutes.

18. The method of claim 17 wherein the time period is in a range extending from about 7 minutes to about 10 minutes.

19. A method for facilitating venous catherization at an extremity of a patient, the method comprising:
    enclosing the extremity within a heater, the heater containing at least one heating element; and
    heating the heating element to a temperature for a given time period, the temperature being in a range extending from about 52 degrees Celsius to about 70 degrees Celsius and the time period being less than about 15 minutes.

20. The method of claim 19 wherein the temperature is about 60 degrees Celsius.

21. The method of claim 19 wherein the time period is in a range extending from about 7 minutes to about 10 minutes.

22. The method of claim 19 further comprising heating the heating element to a second temperature when said time period expires, the second temperature being lower than the temperature.

23. The method of claim 22 wherein the second temperature is in a range extending from about 40 degrees Celsius to about 50 degrees Celsius.

24. The method of claim 23 wherein the second temperature is about 45 degrees Celsius.

25. A heater for heating an extremity of a patient, the heater comprising:
    a flexible heater;
    a flexible shell comprising a first layer and a second layer, the first and second layers being sealed together to enclose the flexible heater, the first layer configured to contact the extremity, wherein the flexible shell is sized to substantially wrap around the extremity of the patient;
    a layer of compressible material positioned between the flexible heater and the second layer;
    a fastening device for holding the flexible shell in place around the extremity, the fastening device being adjustable so the shell can be tightened and loosened, the layer of compressible material configured to press the heater into closer contact with the extremity as the shell is tightened.

26. The heater of claim 25 wherein the layer of compressible material comprises foam rubber.

27. The heater of claim 25 wherein the layer of compressible material comprises foam plastic.

28. The heater of claim 25 wherein the layer of compressible material comprises non-woven polymeric material.

29. The heater of claim 25 further comprising a layer of heat permeable standoff material positioned in between the flexible heater and layer of compressible material.

30. The heater of claim 29 wherein the layer of heat permeable standoff material comprises a layer of metal foil.

31. The heater of claim 25 wherein external surfaces of the first layer and the second layer comprise an antimicrobial material.

32. The heater of claim 25 wherein the flexible heater comprises resistance wire configured as a matrix and attached to a layer of fabric.

33. The heater of claim 25 wherein the flexible heater comprises conductive fabric.

34. The heater of claim 33 wherein the conductive fabric comprises carbon fibers.

35. The heater of claim 33 wherein the conductive fabric comprises a polymeric fabric coated with a conductive material selected from the group consisting of conductive polymers, polypyrrole, carbonized ink or metalized ink.

36. The heater of claim 25 wherein the flexible heater comprises fabric incorporating closely spaced conductive heating elements.

37. The heater of claim 25 wherein the shell includes a first lateral edge, a second lateral edge, a proximal edge and a distal edge, wherein the first lateral edge and second lateral edge are configured to be connected together so that the shell has a tubular shape, the proximal edge forming a open proximal end and the distal edge forming closed a distal end.

38. The heater of claim 37 wherein the fastening device connects the first lateral edge to the second lateral edge.

39. A heater for heating an extremity of a patient, the heater comprising:
a flexible shell having an inner surface and an outer surface, the flexible shell forming a sidewall of an elongate, generally tubular cavity, the tubular cavity adapted to closely receive the extremity;
a proximal edge of the sidewall forming a proximal opening to the cavity;
side edges of the sidewall together forming a side opening to the cavity;
a distal edge of the sidewall forming a permanently closed end, the closed end trapping a distal end of the extremity when the extremity is inserted into the cavity through at least one of the proximal and side openings;
a flap that connects the side edges together to close the side opening; and
at least one flexible heating element enclosed between the inner surface and the outer surface of the flexible shell, wherein the flexible heating element heats to a temperature in a range extending from about 52 degrees Celsius to about 70 degrees Celsius.

40. The heater of claim 39 wherein the inner surface and outer surface comprise water-resistant materials.

41. The heater of claim 39 wherein an antimicrobial material is provided on the inner surface and outer surface.

42. The heater of claim 39 further comprising a layer of compressible material positioned in between the at least one heating element and the outer surface of the shell.

43. A heater for heating an extremity of a patient, the heater comprising:
a flexible shell having an inner surface and an outer surface, the flexible shell forming a sidewall of an elongate, generally tubular cavity, the tubular cavity adapted to closely receive the extremity;
a proximal edge of the sidewall forming a proximal end opening into the cavity;
first and second side edges of the sidewall, each side edge extending distally from the proximal edge and together forming a side opening into the cavity, the side opening extending along a proximal portion of the cavity;
a flap extending laterally from a proximal portion of the second side edge and being adapted to join the second side edge to the first side edge in order to close the side opening into the cavity;
a distal edge closing off a distal portion of the cavity; the distal edge extending longitudinally from the side opening to a distal end of the cavity and then laterally around the distal end of the cavity; and
at least one flexible heating element enclosed between the inner surface and the outer surface of the flexible shell, wherein the flexible heating element heats to a temperature in a range extending from about 52 degrees Celsius to about 70 degrees Celsius.

\* \* \* \* \*